(12) United States Patent
Koehler et al.

(10) Patent No.: US 9,412,184 B2
(45) Date of Patent: Aug. 9, 2016

(54) REGULARIZED PHASE RETRIEVAL IN DIFFERENTIAL PHASE-CONTRAST IMAGING

(75) Inventors: Thomas Koehler, Norderstedt (DE); Ewald Roessl, Henstedt-Ulzburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 194 days.

(21) Appl. No.: 13/820,179

(22) PCT Filed: Sep. 1, 2011

(86) PCT No.: PCT/IB2011/053838
§ 371 (c)(1),
(2), (4) Date: Mar. 1, 2013

(87) PCT Pub. No.: WO2012/029048
PCT Pub. Date: Mar. 8, 2012

(65) Prior Publication Data
US 2013/0156284 A1 Jun. 20, 2013

(30) Foreign Application Priority Data
Sep. 3, 2010 (EP) .................................. 10175174

(51) Int. Cl.
*G06K 9/00* (2006.01)
*G06T 11/00* (2006.01)
*A61B 6/00* (2006.01)

(52) U.S. Cl.
CPC .............. *G06T 11/003* (2013.01); *A61B 6/484* (2013.01); *G06T 11/005* (2013.01); *G06T 11/006* (2013.01)

(58) Field of Classification Search
None
See application file for complete search history.

(56) References Cited

U.S. PATENT DOCUMENTS 7,920,673 B2 * 4/2011 Lanza et al. .................... 378/62
2010/0027739 A1 2/2010 Lanza et al.
(Continued)

FOREIGN PATENT DOCUMENTS

WO 2008102654 A1 8/2008

OTHER PUBLICATIONS

Wu et al NPL: "Phase retrieval from one single phase contrast x-ray image" Department of Radiology, Optical Society of America, 2009.*

(Continued)

*Primary Examiner* — Bhavesh Mehta
*Assistant Examiner* — Oneal R Mistry

(57) ABSTRACT

The present invention relates to differential phase-contrast imaging of an object (108). When reconstructing image information from differential phase-contrast image data, streak-like artefacts (502) may occur. The artefacts (502) may substantially reduce legibility of reconstructed image data. Accordingly, it may be beneficial for removing or at least suppressing said artefacts (502). Thus, a method (400) for regularized phase retrieval in phase-contrast imaging is provided comprising receiving (402) differential phase-contrast image data of an object (108); generating (404) reconstructed image data of an object (108) and presenting (406) reconstructed image data of the object (108). The differential phase-contrast image and the reconstructed image data comprise a two-dimensional data structure having a first dimension and a second dimension. Generating reconstructed image data comprises integration of image data in one of the first dimension and the second dimension of the data structure. A gradient operator is determined in the other one of the first dimension and second dimension of the data structure and the data structure is employed for reconstructing image data resulting in a reduction of artefacts (500) within the reconstructed image data.

24 Claims, 5 Drawing Sheets

(56) References Cited

U.S. PATENT DOCUMENTS

2010/0177864 A1* 7/2010 Donath et al. ............... 378/16
2012/0099702 A1* 4/2012 Engel .................. A61B 6/00
378/62

OTHER PUBLICATIONS

Tim Weitkamp, Ana Diaz, Christian David. "X-ray phase imaging with a grating interferometer." Optics Express, Optical Society of America, Washington DC, pp. 6296-6304. Aug. 8, 2005, vol. 13, No. 16.

Peter Bartl, Jurgen Durst, Wilhelm Haas, Eckhard Hempel, Thilo Michel, Andre Ritter, Thomas Weber, Gisela Anton. "Simulation of X-ray phase-contrast computed tomography of a medical phantom comprising particle and wave contributions." Proc of SPIE, vol. 7622, 76220Q-1.

Heinz W. Engl, Wilhelm Grever. "Using the L-curve for determining optimal regularization parameters". Numerische Mathematik. 69: 25-31 (1994).

Zhihua Qi, Joseph Zambelli, Nicholas Bevins, Guang-Hong Chen. "A novel method to reduce data acquisition time in differential phase contrast: computed tomography using compressed sensing." Medical Imaging 2009, Physics of Medical Imaging. Proceedings of SPIE, vol. 7258, Jan. 1, 2009. vol. 2584A-1-72584A-8.

Jean-Baptiste Thibault, Ken D. Sauer, Charles A. Bouman, Jiang Hsieh. "A three-dimensional statistical approach to improved image quality for multislice helical CT." Medical Physics, vol. 34, No. 11, Nov. 2007, pp. 4526-4544.

Sangtae Ahn, Jeffrey A. Fessler. "Globally convergent image reconstruction for emission tomography using relaxed ordered subsets algorithms." IEEE Transactions on Medical Imaging. vol. 22 No. 5, pp. 613-626, May 2003.

* cited by examiner

REGULARIZED PHASE RETRIEVAL IN DIFFERENTIAL PHASE-CONTRAST IMAGING

FIELD OF THE INVENTION

The present invention relates to X-ray imaging technology in general.

More particularly, the present invention relates to differential phase-contrast imaging.

In particular, the present invention relates to a method for regularized phase retrieval in phase-contrast imaging, an apparatus for regularized phase retrieval in phase-contrast imaging, an X-ray system comprising an apparatus according to the present invention, the use of an apparatus according to the present invention in one of an X-ray system and a CT system, a computer-readable medium, and a program element.

BACKGROUND OF THE INVENTION

In transmission X-ray image acquisition, an object to be examined, e.g., a patient, is arranged between an X-ray generating device, for example an X-ray tube, and an X-ray detector.

X-ray radiation emanating from the X-ray generating device penetrates the object to be examined and subsequently arrives at the X-ray detector for acquiring image information, which may later then be reconstructed into an X-ray image for presentation. The inner structure of the object, e.g., the tissue structure, provides spatial attenuation of the X-radiation penetrating the object. Accordingly, the X-ray detector is registering the spatially attenuated X-ray radiation.

Certain objects may attenuate X-ray radiation only to a smaller extent or may rather uniformly attenuate the X-ray beam resulting in an acquired X-ray image having low contrast.

However, even objects imposing only a small amount of attenuation of an X-ray beam penetrating the object, a phase of a wave front of X-ray radiation may be influenced to a rather large extent by the same object.

Accordingly, phase-contrast imaging may be employed for obtaining image information of an object with enhanced contrast.

In phase-contrast imaging, an X-ray source together with a so-called source grating element arranged adjacent to the X-ray source generates at least partly spatially coherent X-ray radiation. Coherent X-ray radiation penetrating the object may allow a subsequent retrieval of phase information.

Since a phase of a wave may not be measured directly, a further grating element, a so-called phase grating, is employed, arranged between the object to be examined and the X-ray detector. The phase grating allows for a conversion of a phase-shift to an intensity modulation by interference of a plurality of waves, which intensity modulation may then be detectable by an X-ray detector.

However, an interference pattern generated by employing a phase grating only may be too small for a current X-ray detector to be precisely detectable, due to a lack of spatial resolution of the X-ray detector. Here, an additional grating element, a so-called analyzer grating, may be employed, which is arranged between the phase grating element and the X-ray detector in the vicinity of the X-ray detector. The analyzer grating provides an interference pattern, which is large enough to be detectable by a current X-ray detector.

To obtain appropriate phase-contrast image information, phase stepping is conducted for obtaining a plurality of phase-contrast projections. In phase stepping, one of the source grating element, the phase grating element and the analyzer grating element is displaced laterally with respect to the other gratings and the X-ray detector element by a fraction of the respective grating pitch, e.g., a fourth, sixth, eighth of the grating pitch of, e.g., the phase grating. Image acquisition and lateral displacement is repeated, e.g., four, six, or eight times, for acquiring a plurality of phase contrast projections, constituting together a phase stepping interval.

In differential phase-contrast imaging, the first derivative of a phase front perpendicular to the grating direction of a grating element, i.e., the extension of the barrier regions and the trench regions of the grating structure, is detected, thus measured, by the X-ray detector. Due to the grating structure, the acquired image information may be considered to be highly asymmetric with edges being enhanced in particular in one direction, i.e., the direction perpendicular to the grating direction. The direction parallel to the grating direction may not be enhanced.

For reconstructing image information, an integration procedure along the lines of differentiation, i.e., perpendicular to the grating structure, may result in image information having streak-like artefacts or streaks due to noise or other errors, which are arranged locally in the differential image information and which may propagate along the line of reminder of the image data.

Thus, it may be beneficial to provide means for reducing or even removal of said streak-like artefacts.

Phase-contrast imaging is described in both Weitkamp T., Diaz A., David C. et al.: "X-ray phase imaging with a grating interferometer"; Optics Express 6296, 8. August 2005/vol. 13, no. 16 as well as Bartl P., Durst J., Haas W. et al. "Simulation of X-ray phase-contrast computed tomography of a medical phantom comprising particle and wave contributions", Proc of SPIE vol. 7622 76220Q-1.

Determining regularization parameter is described in Engl H. W. and Greyer W.: "Using the L-curve for determining optimal regularization parameters"; Numer. Math. 69: 25-31 (1994).

SUMMARY OF THE INVENTION

One aspect of the present invention may be seen in employing regularization methods known for the solution of ill-posed problems for reducing image artefacts.

Accordingly, a method for regularized phase retrieval in phase-contrast imaging, an apparatus for regularized phase retrieval in phase-contrast imaging, an X-ray system comprising an apparatus according to the present invention, the use of an apparatus according to the present invention in one of an X-ray system and a CT system, a computer-readable medium as well as a program element according to the independent claims are provided.

Preferred embodiments may be taken from the dependent claims.

These and other aspects of the present invention will become apparent from and elucidated with reference to the embodiments described hereinafter.

Exemplary embodiments of the present invention will be described below with reference to the following drawings.

The illustration in the drawings is schematic. In different drawings, similar or identical elements are provided with similar or identical reference numerals.

The figures are not drawn to scale, however may depict qualitative proportions.

DETAILED DESCRIPTION OF EMBODIMENTS

Figure 1:
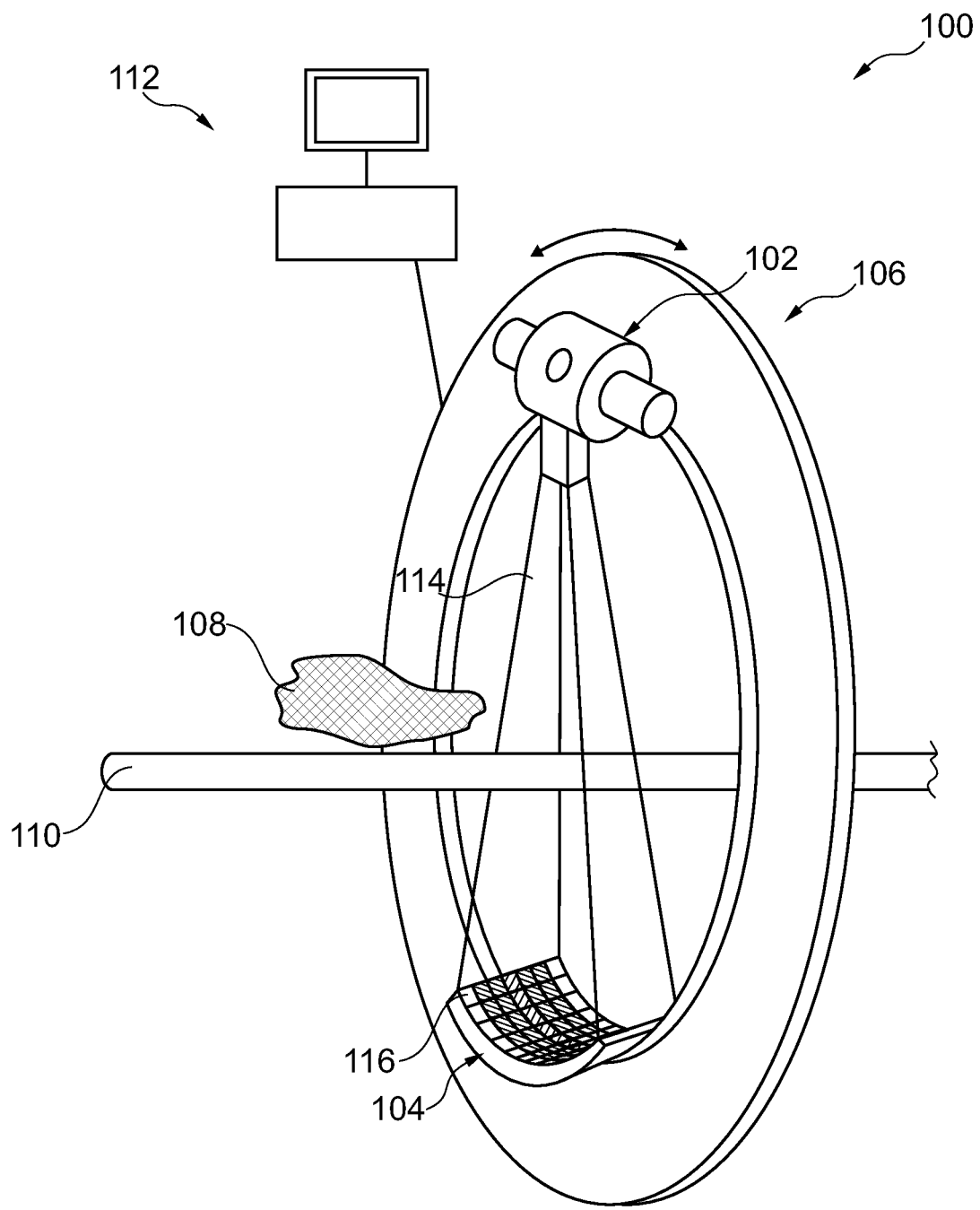
FIG. 1 shows an exemplary embodiment of an X-ray system according to the present invention.

The present invention applies regularization methods for the solution of ill-posed problems to the problem of artefact suppression when reconstructing X-ray images from differential phase-contrast image data acquired employing a differential phase-contrast imaging system.

For the following explanations, without loss of generality, it is assumed that the acquired two-dimensional image information is image information comprising an N×N matrix image structure. In other words, the two-dimensional image comprises as many pixels in an image column as in an image row, thus resulting in a quadratic image. Accordingly, the X-ray detector element employed for acquiring said image data may, e.g., comprise 512×512 or 1024×1024 single individual pixel elements.

Further, it is assumed that the image information to be reconstructed comprises a matrix form of N×(N+1).

However, it is to be understood that the following explanations may also be applied to image data having a substantially different pixel structure and a person skilled in the art may readily adapt the following teachings to the actually occurring image data size or shape.

For the following explanations, we assume that streak-like artefacts occur as horizontal streaks resulting from a grating structure aligned vertically with regard to the image information. Furthermore, without loss of generality, it is assumed that the direction of differentiation is along image rows. Rows of the image data are referred to by index i while columns are referred to by index j.

The measured differential image data is referred to as two-dimensional image data $d_{i,j}$ while the desired two-dimensional image information, i.e., the reconstructed two-dimensional image information, is denoted as $g_{i,j}$.

For the application of regularization methods, the row by row integration problem is reformulated to constitute a linear reconstruction problem. The differentiation operation may be considered a forward problem, which may be expressed as a relation between g and d in accordance with equation 1.

$$d_{i,j} = g_{i,j+1} - g_{i,j} \qquad \text{Equation 1}$$

In accordance with equation 1, a linear relationship between g and d is given. Thus, the two-dimensional image data g and d may be represented as one-dimensional vectors while the forward operation may be formulated as matrix A in accordance with equation 2.

$$d = A \cdot g \qquad \text{Equation 2}$$

Since image information g is the image information to be reconstructed from the measured image data d or the measured vector d, the reconstruction operation may be considered estimating g from the measured vector d.

With regard to the vector notation, single subscript indices to d and g, e.g., $d_k$, may be employed to identify single elements of the respective vectors d and g.

The indices are mapped according to the relation k(i,j)= Ni+j or vice versa j(k)=k mod N, i(k)=integer part of (k/N). Matrix A is then a sparse matrix with $$A_{k,l} = \begin{cases} 1 & \text{for } j(k) = j(l) \text{ and } i(k) = i(l) + 1 \\ -1 & \text{for } j(k) = j(l) \text{ and } i(k) = i(l) \\ 0 & \text{else} \end{cases}$$

For reducing streak-like artefacts, e.g., horizontal streak artefacts, a gradient operator may be employed, which penalizes, i.e., reduces, gradients in the second dimension of the two-dimensional image data different from the dimension of integration, i.e., different from the dimension in which the integration is conducted.

Accordingly, the gradient operator may be defined in accordance with equation 3.

$$(\nabla_z g)_{i,j} = g_{z+1,j} - g_{i,j} \qquad \text{Equation 3}$$

Thus in case the integration operation is conducted within the detector row i of the two-dimensional image data, the gradient operator operates on each column j of the two-dimensional image data.

Like the forward operator matrix A, the gradient operator $\nabla_z$ may be understood to be a linear operator operating on a one-dimensional vector g. The desired image information g may thus be reconstructed by solving the minimization problem in accordance with equation 4.

$$\|A \cdot g - d\|^2 + \lambda \cdot \|\nabla_z g\|^2 = \min. \qquad \text{Equation 4}$$

A regularization parameter λ may be employed for controlling a degree of smoothness that shall be obtained, i.e., an amount of reduction of streak artefacts.

The regularization parameter λ may be required to be found empirically, e.g., by interactive adaptation of λ by a user, who is visually inspecting the reconstructed image data in dependence on λ. The operator may thus interactively control the regularization parameter until a preferred reconstructed image is obtained. Possible values of the regularization parameter λ are real positive values. λ may also be determined by employing the L-curve or by the discrepancy principle by Morozov as described in Engl H. W.

Equation 4 may be considered to be a penalized maximum likelihood reconstruction algorithm. For obtaining a more general form, two generalizations may be employed.

First, the measured data $d_k$ may be considered to be Gaussian distributed random variables with variances $\sigma_k^2$. Even more generalized, a noise co-variance matrix $C_{kl}$ may be employed with the diagonal elements $C_{kk}$ corresponding to $\sigma_k^2$.

Secondly, gradients in z-direction may be penalized differently by a potential function $\Psi((\nabla_z g)_k)$.

For obtaining a unique solution for the minimization problem, the potential function employed may be required to be convex.

According potential functions may be one of the quadratic penalty, the Huber penalty or Huber loss function according to equation 5 or the generalized Gaussian Markov random field according to equation 6

$$\psi_\sigma(x) = \begin{cases} \dfrac{x^2}{2} & \text{for } |x| < \sigma \\ \sigma \cdot |x| - \dfrac{\sigma^2}{2} & \text{for } |x| \geq \sigma \end{cases} \qquad \text{Equation 5}$$

-continued $$\psi_{p,q,\sigma}(x) = \frac{|x|^p}{1+\left|\frac{x}{c}\right|^{p-q}}$$ Equation 6 where σ>0 in the Huber penalty as well as p, q, and c (with p≥q≥1 and c>0) in the generalized Gaussian Markov random field are empirical parameters, which are selected upfront.

By employing according generalizations, a regularized retrieved phase front may be obtained by solving the minimization problem in accordance with equation 7.

$$(A \cdot g - d)^T \cdot C^{-1} \cdot (A \cdot g - d) + \lambda \cdot \sum_k w_k \psi((\nabla_z \cdot g)_k) = \min.$$ Equation 7

In equation 7, additional weighting factors $w_k$ may locally emphasize or de-emphasize the smoothing in the z-direction due to the penalty and are real non-negative values.

Both equation 4 as well as equation 7 may be seen as seeking to reconstruct an additional constant of integration for each detector row, since N+1 values are estimated for each row from just N data samples, which constant may be considered to be responsible for the streak-like artefacts.

In case the object to be examined fits entirely into a single fan of X-ray radiation, the matrix $g_{i,j}$ may also be an N×N size matrix with the integration constant may be fixed to be 0. Specifically, in order to obtain the differential data d, the measured data are referenced to a so-called blank-scan, i.e., a scan without an object. By referencing the scan with the object to the blank-scan, the processing becomes sensitive to just the changes of the wave-front that the object imposes rather than the phase of the wave-front itself. If the object fits entirely into the fan, the first pixel in each detector row is known to be not affected by the object, thus, the change of the phase compared with the blank-scan is zero.

Penalizing, i.e., reducing the gradients in a direction, e.g., the z-direction, may be considered to be very efficient for suppressing streak-like artefacts, in particular horizontal streaks. The streak-like artefacts may be considered to create a gradient over the entire image with a penalty adding up quickly to a substantial value. Accordingly, a streak artefact may be removed by adjusting only a single estimated measured value, i.e., the data penalty term may not change as quickly as the penalty term. This can be easily seen considering as an example the case, where the noise in the data d is dominated by an outlier, i.e., an unusually large noise value, in the data $d_{21}$. By standard phase integration, i.e by estimating g according to $g_{i,j} = \Sigma_{j'=1}^{j} d_{i,j'}$, the single outlier is propagated by the sum throughout the entire row and thus this outlier will contribute to the gradient in z for a large number of detector pixels.

It is to be understood that the application of methods known from the field of inverse, ill-posed problems is neither known nor evident for reducing artefacts within image information, since the actual reconstruction is mathematically not an ill-posed problem but a well-posed problem.

Now referring to FIG. 1, an exemplary embodiment of an X-ray system according to the present invention is depicted.

An X-ray system 100, exemplarily depicted as CT system 100, comprises an X-ray generating device 102, e.g. an X-ray tube, and an X-ray detector 104 comprising individual detector pixel elements 116. X-ray detector element 104 is exemplarily depicted as a two-dimensional array of detector pixel elements 116.

Both the X-ray generating device 102 and the X-ray detector 104 are arranged on a gantry 106 opposing one another. Gantry 106 allows rotation of both the X-ray generating device 102 and the X-ray detector 104 about an axis. X-ray radiation 114 is generated by X-ray generating device 102 and subsequently arriving at X-ray detector 104. X-ray generating device 102 may further comprise a source grating element $G_0$ 202, not depicted in FIG. 1, for generating at least partly spatially coherent X-ray radiation 114 for differential phase-contrast imaging. Further grating elements like e.g. a phase grating element $G_1$ 204 as well as an analyzer grating element $G_2$ 206 are not depicted in FIG. 1.

An object 108 to be examined is arranged on a support 110 adapted to allow moving and placing the object 108 within X-ray beam 114.

A processing system 112 is communicatively coupled to X-ray system 100 for controlling an image acquisition procedure, for reconstructing image data and/or for subsequent presentation, e.g. display, of reconstructed image information.

Figure 2:
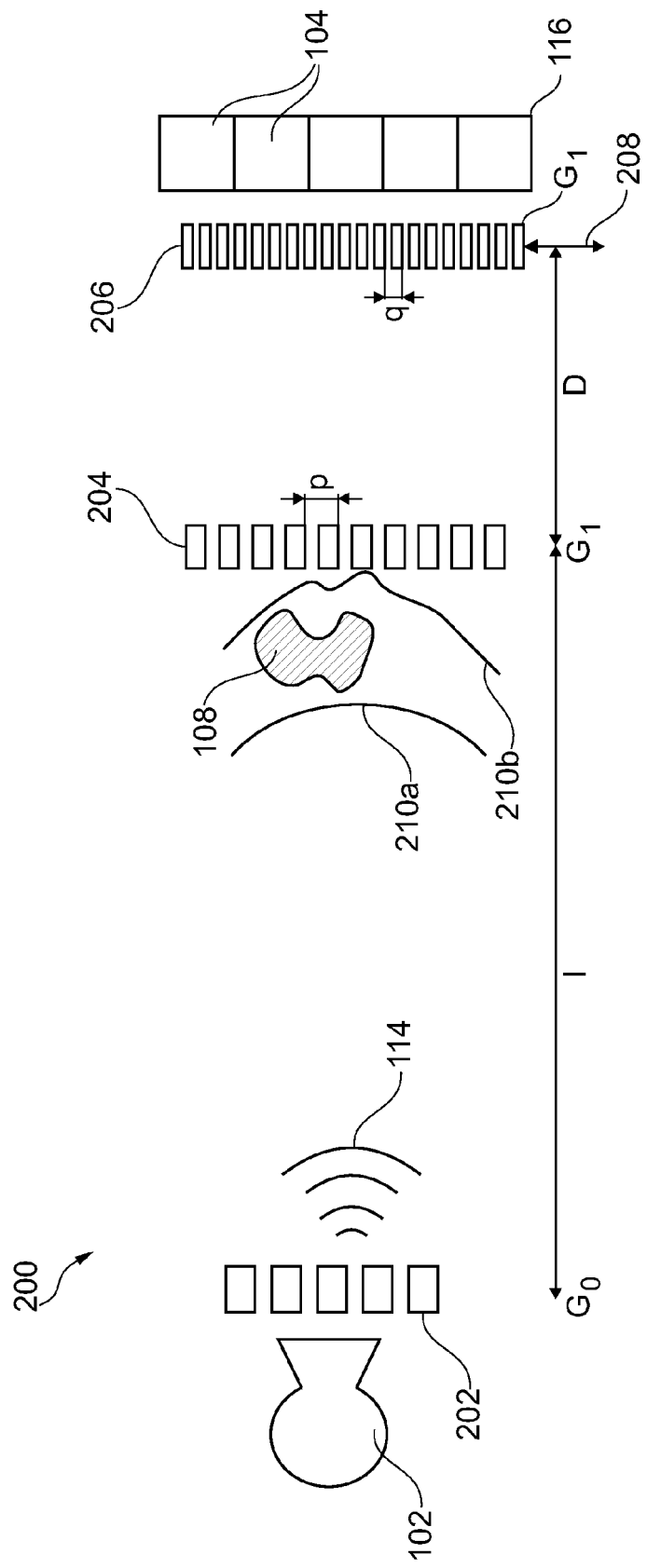
FIG. 2 shows an exemplary embodiment of a differential phase-contrast imaging system according to the present invention.

Now referring to FIG. 2, an exemplary embodiment of a differential phase-contrast imaging system according to the present invention is depicted.

A source grating element $G_0$ 202 is schematically arranged in the vicinity of X-ray generating device 102 for generating at least partly spatially coherent X-ray radiation 114. Source grating element $G_0$ 202 is spaced apart from phase grating element $G_1$ 204 by distance l.

Object 108 is arranged between the X-ray generating device 102 and phase grating element $G_1$ 204. Apparatus 200, a phase-contrast imaging system 200, further comprises an analyzer grating element $G_2$ 206 spaced apart from phase grating element $G_1$ 204 by distance D. Analyzer grating element $G_2$ 206 is arranged in the vicinity of X-ray detector element 104 comprising individual detector pixel elements 116.

A wave front 210a is arriving at object 108, having a uniform phase relationship in accordance with coherent X-ray radiation. After passage of object 108, the uniform phase relationship may have been influenced, as depicted by wave front 210b. After passing through phase grating element $G_1$ 204 and analyzer grating $G_2$ 206, an interference pattern is projected on the X-ray detector element 104 and its individual detector pixel element 116.

An actuator element 208 is exemplarily arranged at analyzer grating element $G_2$ 206 for displacement of analyzer grating element $G_2$ 206 about a fraction of pitch p of phase grating element $G_1$ 204 for acquisition of individual phase-contrast projections during phase stepping, i.e., having individual phase stepping states in a single phase stepping acquisition interval.

Actuator element 208 may also be arranged at one of the phase grating element $G_1$ 204 and the source grating element $G_0$ 202.

Figure 3:
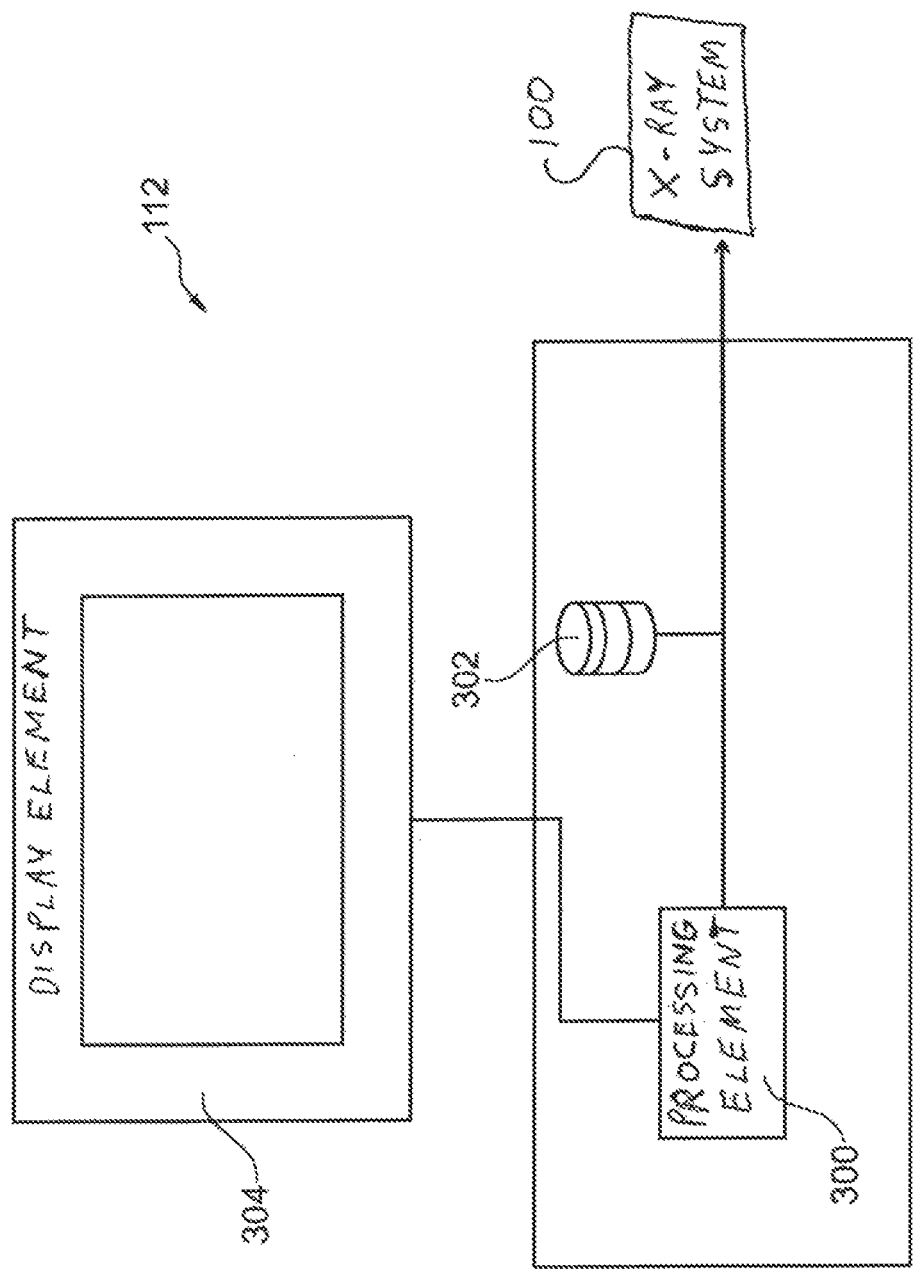
FIG. 3 shows an exemplary embodiment of an apparatus for regularized phase retrieval in phase-contrast imaging according to the present invention.

Now referring to FIG. 3, an exemplary embodiment of an apparatus for regularized phase retrieval in phase-contrast imaging according to the present invention is depicted.

Processing system 112 exemplarily comprises processing element 300, which is attached to a storage element 302 and a display element 304.

Processing system 112 is communicatively coupled with X-ray system 100 for controlling the X-ray system, for reconstructing acquired image information and/or for presenting reconstructed image information, e.g., displaying reconstructed image information on display 304.

However, presenting reconstructed image information may also be understood as providing said reconstructed image information to a further processing system or display system and/or storing reconstructed image information locally, e.g., within storage element 302, or externally in a further storage system, e.g., for long-term storage and archiving.

Processing element 300 is adapted to carry out the method 400 for regularized phase retrieval in phase-contrast imaging, in particular for reconstructing acquired or received phase-contrast image data of an object in accordance with the method 400 of the present invention.

Figure 4:
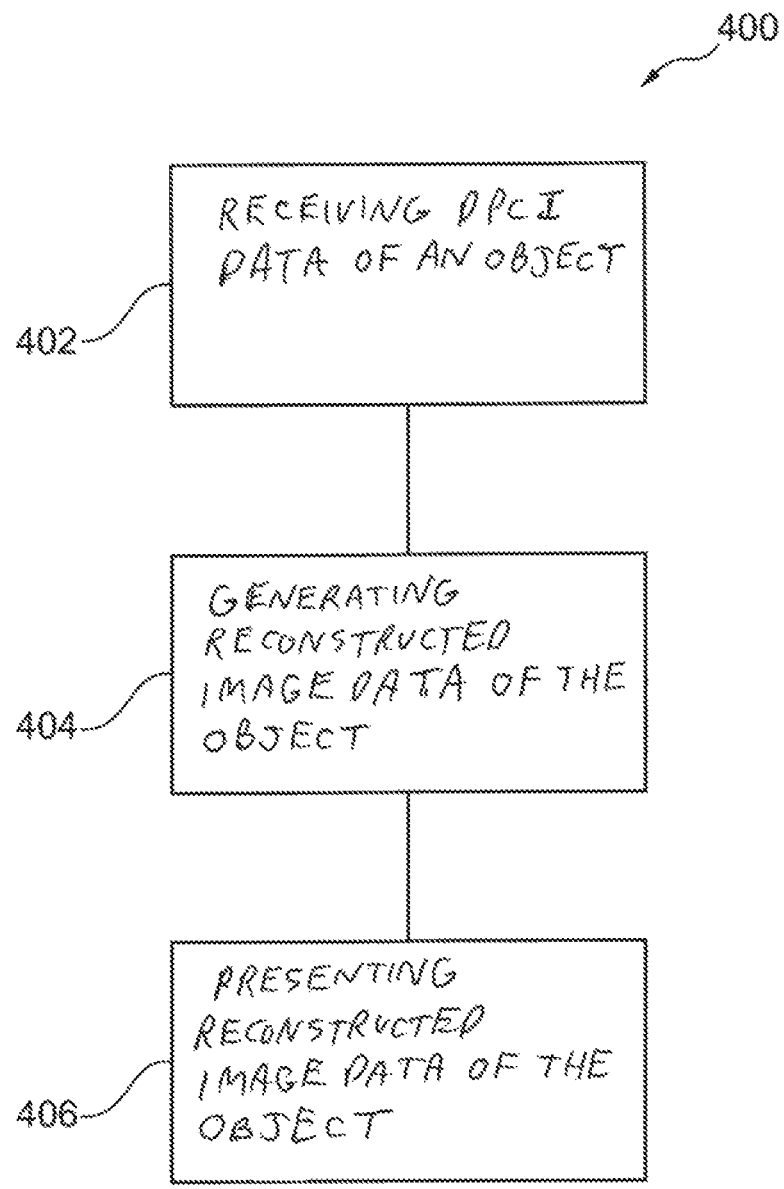
FIG. 4 shows an exemplary embodiment of the method for regularized phase retrieval in phase-contrast imaging according to the present invention.

Now referring to FIG. 4, an exemplary embodiment of the method for regularized phase retrieval in phase-contrast imaging according to the present invention is depicted.

FIG. 4 shows the method 400 for regularized phase retrieval in phase-contrast imaging, comprising receiving 402 differential phase-contrast image data of an object, generating 404 reconstructed image data of the object and presenting 406 reconstructed image data of the object.

The generation of the reconstructed image data may comprise employing regularization methods in accordance with the present invention for recombinant image data in particular for removing or suppressing artefacts like e.g., streak-like artefacts in the reconstructed image data.

Presenting reconstructed image data of object 108 may thus be a display of image information to a user of the X-ray system 100. However, presenting may also comprise storing reconstructed image data for a later display, archival of reconstructed image data, thus permanent or temporal storage of image data and may also comprise providing image data to a further processing system for, e.g., display, storage, or further processing.

Figure 5C:
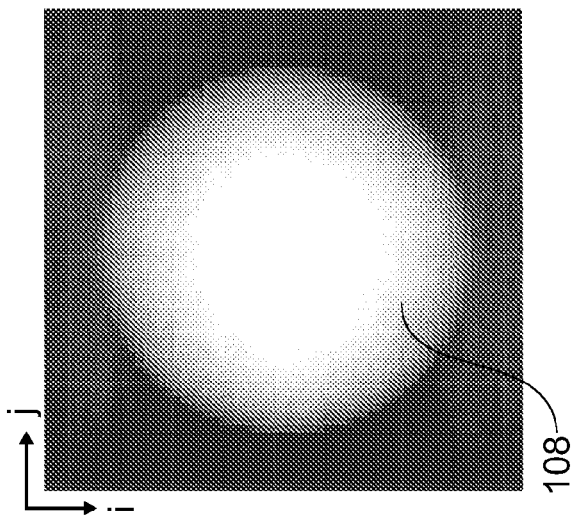
FIGS. 5a-c show an exemplary reconstruction of image information employing differential phase-contrast image data according to the present invention.
Figure 5B:
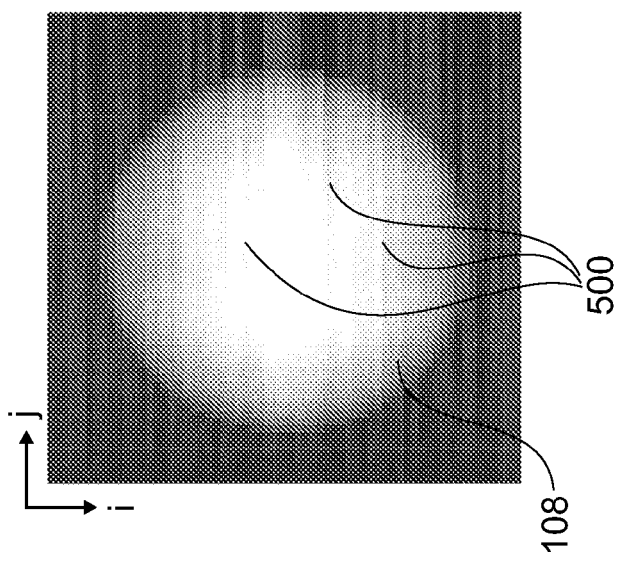
Figure 5A:
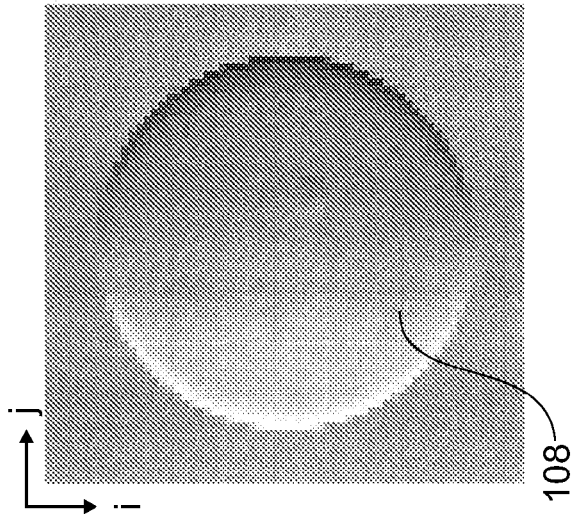

Now referring to FIGS. 5a-c, an exemplary reconstruction of image information employing differential phase-contrast image data according to the present invention is depicted.

In FIG. 5a, two-dimensional differential phase-contrast image data is presented. The image data of FIG. 5a depicts the differential image relationship of individual pixels of the image as acquired by the X-ray detector 104 in differential phase-contrast imaging. While individual columns are referred to with index j, individual rows are referred to with index i.

In FIG. 5a, the grey values of the individual pixels substantially depict a difference in image value with respect to adjacent pixels. E.g., in the background of the circular-shaped object 108 of FIG. 5a, a uniform grey value is present, exemplifying substantially no change of image information with regard to adjacent pixels. Accordingly, in FIGS. 5b and 5c, the corresponding background of object 108 is depicted as black. Light pixel values at the left hemisphere of object 108 depict a rather steep change in image information, either positive or negative. Dark pixel values at the right hemisphere of object 108 exemplifies a substantially similar steep change in the other direction, thus either negative or positive. Image information in FIGS. 5b and 5c are thus obtainable by integration, e.g., along individual rows (i=const), of FIG. 5a.

FIG. 5b depicts a reconstructed image from the differential phase-contrast imaging information of FIG. 5a, employing a common reconstruction algorithm, e.g., an integration operation. Streak-like artefacts 500, in FIG. 5b exemplarily depicted as horizontal streaks are present. Image information of FIG. 5b was obtained from the image information of FIG. 5a by row by row integration of image information of FIG. 5a.

Now when employing method 400 according to the present invention, while reconstructing image information, an X-ray image in accordance with FIG. 5c may be obtained. With the image information of FIG. 5c, in addition to the row by row integration, a gradient operator penalizing gradients in z-direction, i.e., with regard to columns (j=const) is employed. By employing a gradient operator in accordance with the present invention, streak-like artefacts 500 are substantially removed from the reconstructed image data as presented in FIG. 5c. Accordingly by employing a gradient operator in accordance with the present invention, the streak-like artefacts 500 may be reduced or even removed.

It should be noted that the term "comprising" does not exclude other elements or steps and that "a" or "an" does not exclude a plurality. Also, elements described in association with different embodiments may be combined.

It should also be noted, that reference numerals in the claims shall not be construed as limiting the scope of the claims.

LIST OF REFERENCE SIGNS

100 X-ray system
102 X-ray generating device/X-ray source
104 X-ray detector
106 Gantry
108 Object
110 Support
112 Processing system
114 X-ray radiation
200 Differential phase-contrast imaging system
202 Source grating
204 Phase grating $G_1$
206 Analyzer grating $G_2$
208 Actuator element
210a,b Wave front
300 Microprocessor
302 Storage element
304 Display element
400 Method for regularized phase retrieval and phase-contrast imaging
402 Receiving differential phase-contrast image data
404 Generating reconstructed image data
406 Presenting reconstructed image data
500 Streak-like artefacts

The invention claimed is:

1. A method for regularized phase retrieval in phase contrast imaging, comprising receiving differential phase contrast image data of an object ($d_{i,j}$); generating reconstructed image data of the object ($g_{i,j}$); and presenting reconstructed image data of the object ($g_{i,j}$); wherein the differential phase contrast image data and the reconstructed image data comprise a two-dimensional data structure having a first dimension (i) and a second dimension (j); wherein generating reconstructed image data comprises integration of image data in one of the first dimension (i) and the second dimension (i) of the data structure; wherein a gradient operator is determined in the other one of the first dimension (i) and the second dimension (j) of the data structure; and wherein the gradient operator is employed for reconstructing, image data.

2. The method according to claim 1, wherein the reconstructed image data is generated by employing the equation $d_{i,j} = g_{i,j+1} - g_{i,j}$.

3. The method according to claim 1, wherein the gradient operator is determined by the equation $(\nabla_z g)_{i,j} = g_{z+1,j} - g_{i,j}$.

4. The method according, to claim 1, wherein the image data is reconstructed by solving the equation $\|A \cdot g - d\|^2 + \lambda \cdot \|\nabla_z \cdot g\|^2 = \min$.

5. The method according to claim 1, wherein the image data is reconstructed by solving the equation $$(A \cdot g - d)^T \cdot C^{-1} \cdot (A \cdot g - d) + \lambda \cdot \sum_k w_k \Psi((\nabla_Z \cdot g)_k) = \min.$$

6. The method according to claim 5, where $\Psi$, as a potential function, is one of the quadratic penalty, the Huber penalty, and the generalized Gaussian Markov random field.

7. The method of claim 1, the employment of said gradient operator effecting said regularized phase retrieval.

8. The method of claim 7, the regularization serving to reduce, remove or suppress visual artefacts.

9. The method of claim 8, wherein among said artefacts there are streak-like artefacts.

10. The method of claim 1, wherein the employment of said gradient operator is in said other one of the first dimension (i) and the second dimension (j) of the data structure.

11. A non-transitory computer readable medium embodying a computer program for regularized phase retrieval in phase contrast imaging said computer program comprising instructions executable by a processor for performing a plurality of acts, among said plurality there being the acts of:
generating reconstructed image data of the object ($g_{i,j}$); and
presenting the generated data
wherein both the differential phase contrast image data and the reconstructed image data comprise a two-dimensional structure having a first dimension (i) and a second dimension (j);
wherein generating reconstructed image data comprises integration of image data in one of the first dimension (i) and the second dimension (j) of the data structure; and
wherein a gradient operator determined in the other one of the first dimension (i) and the second dimension (j) of the data structure employed for reconstructing image data.

12. The computer readable medium of claim 11, the employment of said gradient operator effecting said regularized phase retrieval, the regularization serving to reduce, remove or suppress visual artefacts.

13. The computer readable medium of claim 12, wherein among said artefacts there are streak-like artefacts.

14. The computer readable medium of clam 11, wherein the employment of said gradient operator is in said other one of the first dimension (i) and the second dimension (j) of the data structure.

15. An apparatus for regularized phase retrieval in phase contrast imaging, comprising:
a storage element for storing received differential phase contrast image data of an object ($d_{i,j}$); and
an image reconstruction processor configured for
generating reconstructed image data at the ($g_{i,j}$); and
presenting, via a display, the generated data;
wherein both the differential phase contrast image data and the reconstructed image data comprise a two-dimensional data structure having a first dimension (i) and a second dimension (j);
wherein generating reconstructed image data comprises integration of image data in one of the first dimension (i) and the second dimension (j) of the data structure; and
wherein a gradient operator determined in the other one of the first dimension (i) and the second dimension (j) of the data structure is employed for reconstructing image data.

16. An X-ray system comprising the apparatus according to claim 15.

17. The system of claim 16, implemented as a computed tomography (CT) system.

18. The apparatus of claim 15, the employment of said gradient operator effecting said regularized phase retrieval, the regularization serving to reduce, remove or suppress visual artifacts.

19. The apparatus of claim 18, wherein among said artefacts there are streak-like artefacts.

20. The apparatus of claim 18, further comprising said display.

21. The apparatus of claim 18, said processor comprising a microprocessor.

22. The apparatus of claim 15, further comprising said display.

23. The apparatus of claim 15, said processor comprising a microprocessor.

24. The apparatus of claim 15, wherein the employment of said gradient operator is in said other one of the first dimension (i) and the second dimension (j) of the data structure.

* * * * *